(12) United States Patent
Becker (10) Patent No.: US 8,500,717 B2
(45) Date of Patent: Aug. 6, 2013

(54) CONNECTION PIECE FOR AN ENTERAL TRANSFER SYSTEM

(75) Inventor: Michael Becker, Knittlingen (DE)

(73) Assignee: Fresenius Medical Care Deutschland GmbH, Bad Homburg V.D.H. (DE)

( * ) Notice: Subject to any disclaimer, the term of this patent is extended or adjusted under 35 U.S.C. 154(b) by 374 days.

(21) Appl. No.: 12/447,017

(22) PCT Filed: Oct. 23, 2007

(86) PCT No.: PCT/EP2007/009156
§ 371 (c)(1),
(2), (4) Date: Aug. 25, 2009

(87) PCT Pub. No.: WO2008/049568
PCT Pub. Date: May 2, 2008

(65) Prior Publication Data
US 2010/0036365 A1    Feb. 11, 2010

(30) Foreign Application Priority Data
Oct. 25, 2006 (DE) .......................... 10 2006 050 212

(51) Int. Cl.
*A61M 25/16* (2006.01)

(52) U.S. Cl.
USPC ........................................... 604/534; 604/539

(58) Field of Classification Search
USPC ................. 604/533–284, 96.01, 164.01, 523, 604/174–180
See application file for complete search history.

(56) References Cited

U.S. PATENT DOCUMENTS

| 4,692,150 A | | 9/1987 | Cianci et al. |
| 4,693,707 A | | 9/1987 | Dye |
| 5,047,021 A | * | 9/1991 | Utterberg ..................... 604/533 |

(Continued)

FOREIGN PATENT DOCUMENTS

| DE | 690 16 889 T2 | 8/1995 |
| WO | 81/01654 A | 6/1981 |

(Continued)

OTHER PUBLICATIONS

International Preliminary Report on Patentability for PCT/EP2007/009156, mailed on May 5, 2009.
International Search Report, PCT/EP2007/009156, mailed Feb. 18, 2008.

*Primary Examiner* — Bhisma Mehta
*Assistant Examiner* — Phillip Gray
(74) *Attorney, Agent, or Firm* — Kenyon and Kenyon LLP (57) ABSTRACT

The present invention relates to a connection piece for an enteral transfer system and to an enteral transfer system with such a connection piece, and also to an arrangement composed of such a transfer system and of an enteral feed probe. The connection piece according to the present invention comprises a distal attachment piece for attachment of a connection piece of a probe tube of an enteral feed probe, and a proximal attachment piece for attachment of the connection tube of a transfer system. The distal attachment piece of the connection piece is conical or is designed in stepped fashion with several portions of different diameter. The distal attachment piece can therefore be releasably connected to the funnel-shaped connection pieces of different diameter of the probe tubes of the known feed probes. The connection piece according to the present invention can be used universally in this respect. The distal attachment piece of the connection piece according to the present invention has a locking element which is designed in such a way that a releasable form-fit connection can be made to a connection piece of a probe tube of an enteral feed probe that has a locking element complementing the locking element of the distal attachment piece.

8 Claims, 5 Drawing Sheets

(56) References Cited

U.S. PATENT DOCUMENTS

| | | |
|---|---|---|
| 5,057,093 A | 10/1991 | Clegg et al. |
| 5,176,415 A * | 1/1993 | Choksi .......................... 285/331 |
| 6,068,617 A | 5/2000 | Richmond |
| 6,802,836 B2 | 10/2004 | Bouphavichith et al. |
| 6,979,322 B2 | 12/2005 | Chu et al. |
| 2005/0033268 A1 | 2/2005 | Decaria |
| 2005/0033269 A1 | 2/2005 | Decaria |

FOREIGN PATENT DOCUMENTS

| | | |
|---|---|---|
| WO | 91/19462 A | 12/1991 |
| WO | 02/02048 A | 1/2002 |
| WO | 02/051494 A1 | 7/2002 |
| WO | 03/055436 A1 | 7/2003 |
| WO | 03/070151 A2 | 8/2003 |
| WO | 2005/016223 A1 | 2/2005 |
| WO | 2005/055919 A1 | 6/2005 |

* cited by examiner

CONNECTION PIECE FOR AN ENTERAL TRANSFER SYSTEM

CROSS REFERENCE TO RELATED APPLICATIONS

This is a 371 national phase application of PCT/EP2007/009156 filed Oct. 23, 2007, claiming priority to German Patent Application No. 10 2006 050 212.4 filed Oct. 25, 2006.

FIELD OF INVENTION

The present invention relates to a connecting piece for an enteral transfer system that has a distal connecting portion for connection to a connecting piece of the flexible tube of an enteral feeding probe, and a proximal connecting portion for connection to a flexible connecting tube of a transfer system. The present invention also relates to a transfer system for enteral feeding having a connecting piece of this kind. What is more, the present invention also relates to an arrangement which comprises a transfer system of this kind and an enteral feeding probe that has a flexible probe tube having a connecting piece for connection to the transfer system.

BACKGROUND OF THE INVENTION

In enteral feeding, a liquid nutrient solution is administered to the patient with an enteral feeding probe. The enteral nutrient solution is made available in a container that is connected to the enteral feeding probe via what is referred to as a transfer system. The enteral transfer system has a flexible probe tube having a proximal and a distal connecting piece. The distal connecting piece is connected to the feeding probe and the proximal connecting piece is connected to the container holding the nutrient solution, thus allowing the nutrient solution to flow out of the container and, via the connecting tube of the transfer system, into the feeding probe.

The container of nutrient solution is generally changed several times a day whereas in the case of the transfer system a change is recommended every 24 hours. The feeding probe can be used for as long as several months.

What have been used in the prior art to connect the connecting tube of the transfer system to the flexible tube of the feeding probe are the known luer lock connectors, thus enabling the transfer system and feeding probe to be connected together without there being any risk of the flexible tube of the feeding probe unintentionally coming loose from the flexible connecting tube of the transfer system during the administration of the nutrient solution. It is however a disadvantage that in enteral administration the known luer lock connections may pose a risk to the patient inasmuch as the luer lock connections used in enteral administration may be confused with those which are used particularly in intravenous administration and in ventilation techniques. If for example an enteral nutrient solution should inadvertently be administered via an intravenously inserted luer lock connection, there is a considerable risk to the patient.

An improvement in safety was achieved in the prior art by giving the enteral transfer system a female distal luer lock connecting piece, whereas the enteral feeding probe has a male luer lock connecting piece. Intravenous probes however have a female luer lock connecting piece, and because of this the possibility of an enteral transfer system being connected directly to the intravenous probe can be ruled out. However, because of the large number of luer lock adapters available which are offered by the various manufacturers, the possibility of mix-ups cannot be entirely ruled out.

As well as the transfer systems and feeding probes which have luer lock connections, what are also known are feeding probes which have a funnel-shaped connecting piece. Various manufacturers offer feeding probes having connecting funnels of different diameters in this case. For a connection to be able to be made to the connecting funnels of the known feeding probes, there are known in the prior art adapters of a stepped form which are generally releasably connected to the connecting tube of the transfer system by means of a luer lock connection.

The known stepped adapters have the advantage that a connection is possible to connect funnels of different diameters. The stepped adapter is plugged into the connecting funnel of the feeding probe and when this is done that section of the stepped adapter whose diameter corresponds to the diameter of the connecting funnel comes into contact with the connecting funnel. The two parts are fixed in this case by the frictional force between the circumferential surfaces of the stepped adapter and the connecting funnel.

Whereas the stepped adapter is generally made of a harder material, the connecting funnel is, as a rule, composed of a softer material to improve the transmission of force. It is a disadvantage that the retaining force between the stepped adapter and the connecting funnel may not be high enough. Particularly when nutrient solutions containing fat or grease are being used there is a risk of the connection unintentionally coming loose. Ageing effects which affect the properties of the material of the connecting funnel and its geometry may also result in a reduced retaining force.

Screwed connections, which are also used in the field of enteral feeding, are known from WO 2005/055919 A1. It is a disadvantage that the known screwed connections are not capable of general use but are confined to the particular feeding probe or transfer system which has appropriate connections.

A connecting piece of stepped form which has a plurality of sections of different diameters onto which an elastic flexible tube can be slid is known for example from U.S. Pat. No. 4,693,707. It is true that a sealed connection to flexible tubes of different diameters can be made with this known stepped adapter, but it is a disadvantage that there is a risk of the flexible tube coming loose from the connecting piece if a tractive stress is applied.

A stepped adapter for use in the field of enteral feeding is known from WO 02/051494 A1. In this case too the risk exists of the flexible tube of the feeding probe unintentionally coming loose.

U.S. Pat. No. 4,692,150 describes an arrangement which comprises a flexible probe tube having a connecting funnel and a flexible connecting tube having a stepped adapter. To secure the stepped adapter in the connecting funnel, this printed publication proposes the use of a securing band which is slid over the junction after the two parts have been plugged together, thus causing the two parts to be held together. The securing band is similarly intended to act as a protection against bacteria. It is however a disadvantage that the use of an additional securing band which has to be slid over the junction after the parts have been plugged together makes handling more difficult.

SUMMARY OF THE INVENTION

One object underlying the present invention is to provide a connecting piece for an enteral transfer system which is capable of being used generally, which is easy to handle, and which makes a secure but releasable connection possible between a transfer system and feeding probe. A further object of the present invention is to provide a transfer system for enteral feeding which is capable of being used generally, which is easy to handle, and which can be connected to a feeding probe without the risk of the connection unintentionally coming loose. It is also an object of the present invention to provide an arrangement, comprising a transfer system and a feeding probe, which is capable of being used generally and which is easy to handle, the feeding probe and transfer system being able to be connected together securely.

The connecting piece according to the present invention for an enteral transfer system has a distal connecting portion for connection to a connecting piece of the flexible tube of an enteral feeding probe, and a proximal connecting portion for connection to the flexible connecting tube of a transfer system.

The distal connecting portion of the connecting piece has either a conical section or a stepped section. In the case of a stepped section, the distal connecting portion may itself have shoulders of different diameters which are conical and/or cylindrical. What is crucial is that the conical or stepped section of the distal connecting piece narrows. The distal connecting portion can therefore be releasably connected to the funnel-shaped connecting pieces of different diameters of the flexible tubes of known feeding probes. Thus, the connecting piece according to the present invention is capable of being used generally.

The distal connecting portion of the connecting piece according to the present invention has a locking element, which is so designed that a positively engaged releasable connection can be made to a connecting piece of a flexible tube of an enteral feeding probe when this latter connecting piece has a locking element which is complementary to the locking element of the distal connecting portion. The locking element may be of different designs. What may be considered as locking elements are all positively engaging releasable connections such as, for example, screwed and plug-in connections and in particular over-fitting caps, screwed joints, bayonet connections or the like.

Thus, a positively engaged releasable connection to a connecting piece of a flexible tube of an enteral feeding probe, which connecting piece has a locking element complementary to the locking element of the distal connecting portion, is possible by virtue of the special design of the distal connecting portion. Additionally, the connecting piece according to the present invention can be connected in a known manner to the funnel-shaped connecting pieces, of different diameters, of known feeding probes.

It is of advantage that, because of the incompatibility of the connecting pieces, the connecting piece according to the present invention rules out the possibility of mix-ups with luer lock connections which are not used for enteral accesses.

In cases where the connecting piece according to the present invention is used to connect up a feeding probe which has a complementary locking element, the said connecting piece makes a connection by positive and frictional engagement which is easily released and which is secured against coming loose unintentionally.

The general use which can be made of the connecting piece according to the present invention leads to a reduction in costs in the provision of different feeding probes and in transfer systems. Also, there are fewer problems involved in the changeover from the known feeding probes having connecting funnels to feeding probes which have a complementary locking element, because it will still be possible for conventional feeding probes to be connected on, at least for a certain transitional period.

The connecting piece according to the present invention combines the advantages of the known luer lock connectors with the advantages of the known connections which do not engage positively but only by friction between funnel-shaped connecting portions and stepped adapters or even conical adapters, but without having to accept their disadvantages.

In a preferred embodiment of the connecting piece according to the present invention, the front section of the distal connecting portion, which section is of the smallest diameter, takes the form of a locking element. In this embodiment, the sealing of the connecting pieces of the feeding probe and transfer system takes place particularly at the end-face of the distal connecting portion, which bears against the end-face of the connecting piece with a seal. Basically however it is also possible for the locking element to be provided in the rear or center region of the distal connecting portion, which connecting portion is either conical, or stepped in a plurality of sections.

In an alternative and particularly preferred embodiment, the front section of the distal connecting piece takes the form of a connecting cone and the section of the distal connecting portion which follows on from the connecting cone takes the form of a locking element. In this case, the sealing takes place by virtue of the fact that the connecting cone of the connecting portion engages in a bore which is of a corresponding conicity in the connecting piece of the feeding probe.

In both cases, a sealed but easily releasable connection is made between the flexible tube and the flexible connecting tube of the feeding probe and transfer system, respectively.

A particular embodiment makes provision for the locking element of the distal connecting portion to take the form of a screwed connecting element, and preferably that of a cylindrical or conical connecting element having an outside thread. It is however also possible for the screwed connecting element to have an inside thread. A cylindrical section may for example be provided with a rib which extends round in a helix or with a helical groove. The section may also be conical, in which case the height of the rib or the depth of the groove is of a size, over the length of the section, such that the distance between, respectively, the outer face of the rib and the floor of the groove and the axis of the cylindrical or conical section remains the same over this length. The connecting piece of the flexible tube of the probe is then of whichever form is complementary.

A further embodiment makes provision for the locking element of the distal connecting portion to take the form of a bayonet-type connecting element. The bayonet-type connecting element is preferably a cylindrical connecting element whose circumferential surface has a groove, the groove preferably having an axially extending section from which a section which extends around part of the circumference of the circumferential surface follows on. It is however also possible for the cylindrical connecting element to be the bayonet-type connecting element complementary to the above configuration that has a projection that engages in a groove.

Provision may be made for any of the connecting techniques which are known to the person skilled in the art as bayonet connections. The bayonet-type connecting element may be provided in the rear, centre or front region of the distal connecting portion. The connecting piece of the flexible probe tube is then formed in turn in whichever way is complementary.

In an alternative and particularly preferred embodiment, the locking element of the distal connecting portion does not take the form of a screwed connecting element on the stepped or conical section of the distal connecting portion. Rather the locating element takes the form of a screwed cap having an inside thread, which screwed cap encloses the conical section of the distal connecting portion for at least part of its length, or may enclose a stepped section for at least part of its length if the distal connecting portion has a stepped section rather than a conical one. The screwed cap may be an integral part of the distal connecting portion or may be rotatable about the axis of the distal connecting portion.

Rather than a screwed cap, what may also be provided is a cap which is inserted onto the connecting piece of the flexible probe tube as a good fit. It may for example be fixed in place on the connecting piece of the flexible probe tube by a clamping or latching action.

The cap may also take the form of a bayonet-type connection, in which case either the projection of the bayonet-type connection which engages in the groove, or its groove, may be provided in the distal connecting portion.

It goes without saying that in the different embodiments of the distal connecting piece the connecting piece of the flexible probe tube is, in turn, of a complementary form. The connecting piece of the flexible probe tube may for example take the form of a connecting funnel, in which case an outside thread for a screwed connection, or whatever is the complementary mating part of a bayonet-type connection, may be provided on the outside of the funnel.

The proximal connecting portion of the connecting piece according to the present invention may take the form of a connecting portion for making a releasable connection to a complementary connecting portion of the transfer system, and in particular the form of a luer lock connecting portion. It is possible in this way for the connecting piece according to the present invention to be handled and used in the same way as the known stepped adapters which are connected to the luer lock connecting portions of known transfer systems. Preferably however the connecting piece according to the present invention is connected directly to the flexible tube of the feeding probe, such for example as by being adhesive-bonded and/or welded.

The transfer system according to the present invention comprises the connecting piece according to the present invention and an enteral transfer system, in which case the connecting piece according to the present invention may take the form of an adapter for the luer lock connecting portion of the enteral transfer system or may be connected solidly to the flexible connecting tube of the enteral transfer system.

The arrangement according to the present invention comprises the transfer system according to the present invention and an enteral feeding probe which can be connected to the connecting piece of the transfer system according to the present invention.

BRIEF DESCRIPTION OF THE DRAWINGS

Various embodiments of the present invention will be explained in detail below by reference to the drawings. In the drawings.

DETAILED DESCRIPTION OF THE DRAWINGS

Figure 1:
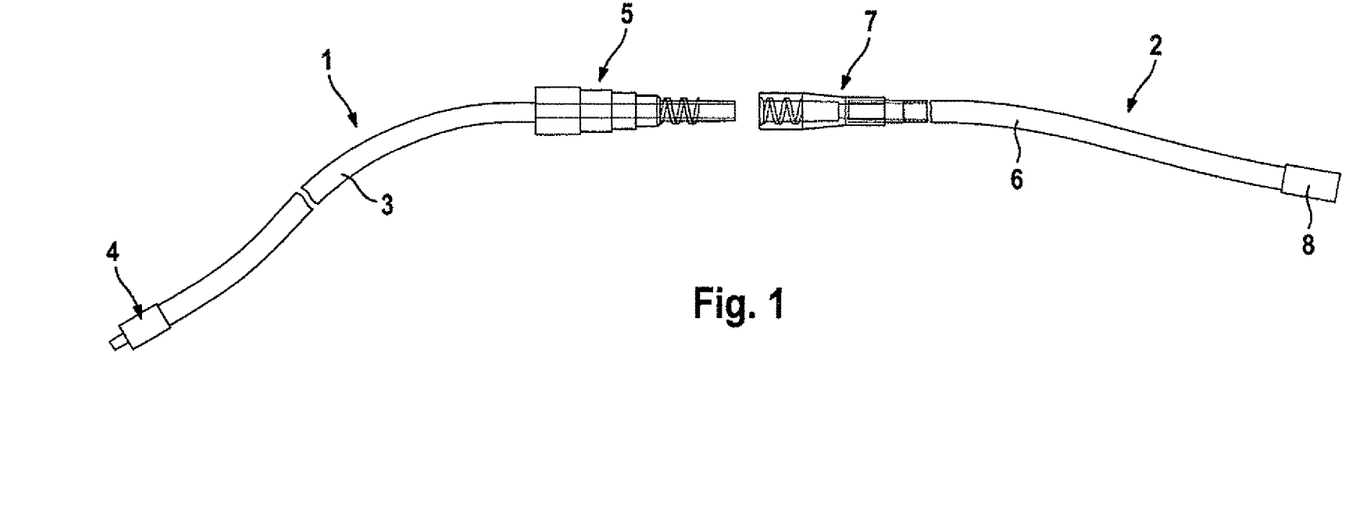
FIG. 1 shows an arrangement comprising a transfer system and an enteral feeding probe.

FIG. 1 is a simplified view showing an arrangement comprising a transfer system 1 for enteral feeding and an enteral feeding probe 2, the two of which are connected together to allow an enteral nutrient solution to be administered to the patient from a nutrient solution container (not shown).

Because enteral transfer systems and feeding probes are known per se to the person skilled in the art, the description will be confined in essence to the parts which are relevant to the present invention.

The transfer system 1 has a flexible connecting tube 3, which has a proximal connecting piece 4 at its proximal end and a distal connecting piece 5 at its distal end. The proximal connecting piece 4 is used to connect the transfer system 1 to a nutrient solution container (not shown) whereas the distal connecting piece 5 is used to connect to the feeding probe 2.

The feeding probe 2 has a flexible tube 6, which has a proximal connecting piece 7 at its proximal end and an end-piece 8 which leads into the patient at its distal end. The proximal connecting piece 7 of the feeding probe 2 is connected to the distal connecting piece 5 of the transfer system 1.

In what follows, various embodiments of the connecting pieces of the transfer system 1 and feeding probe 2 will be described in detail.

Figure 2A:
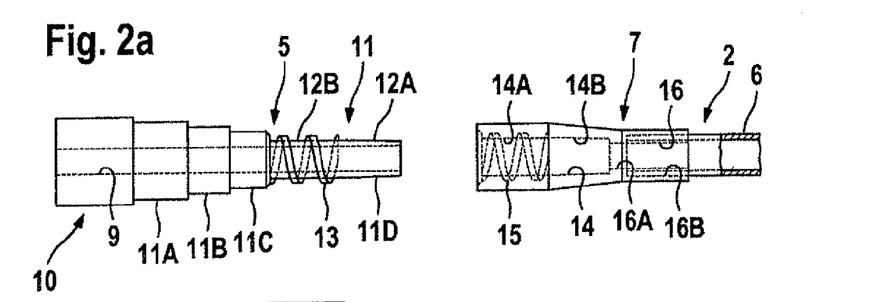
FIGS. 2a and 2b are enlarged views of the connecting pieces of the transfer system and feeding probe shown in FIG. 1, before and after the making of a connection between the transfer system and the feeding probe.
Figure 2B:
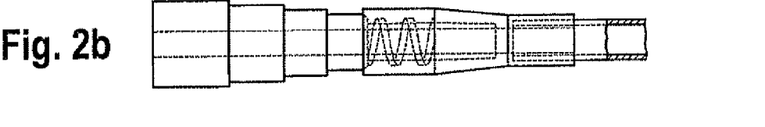

FIGS. 2a and 2b are enlarged views of a first embodiment of the proximal connecting piece 5 of the transfer system 1 and of the distal connecting piece 7 of the feeding probe 2. FIG. 2a shows the connecting pieces before they are screwed together and FIG. 2b shows them after they are screwed together.

The connecting piece 5 is a tubular part made of plastic material that is produced by the injection molding process. The passage 9 that is formed in the connecting piece is shown in broken lines. The connecting piece 5 has a proximal connecting portion 10, which in FIGS. 2a and 2b is the left-hand sub-division of the connecting piece. The distal end of the flexible connecting tube 3 of the transfer system 1 is solidly connected to the proximal connecting portion 10. For this purpose, the end of the flexible tube may, for example, be inserted in a bore in the proximal connecting portion 10 and may be adhesive-bonded and/or welded to the connecting portion.

To allow the feeding probe 2 to be connected, the connecting piece of the transfer system 1 has a distal connecting portion 11, which in FIGS. 2a and 2b is the right-hand sub-division of the connecting piece 5. The distal connecting portion 11 is a stepped sub-division having a plurality, totaling four in the present embodiment, of sections 11A, 11B, 11C, 11D of different diameters, with the diameters decreasing in the direction of the front end. The front section 11D is approximately twice as long as the rear sections 11A, 11B, or 11C.

The front section 11D comprises a front, conical, sub-division 12A and a rear, cylindrical, sub-division 12B which is provided with an outside thread 13. The conical sub-division forms a connecting cone which can be slid into a bore of corresponding conicity in the connecting piece 7 of the feeding probe 2, whereas the cylindrical sub-division 12B having the outside thread 13 forms a locking element, thus enabling a positively engaged connection to be made to a complementary locking element belonging to the connecting piece 7 of the feeding probe 2. The connecting piece 7 of the feeding probe 2 is likewise a tubular part made of plastic material, which can be produced by the injection molding process. The connecting piece 7 has a bore 14 that is shown in broken lines and that has a cylindrical front section 14A and a slightly conical rear section 14B. The cylindrical section 14A of the bore 14 in the connecting piece 7 has an inside thread 15 which is shown in broken lines and which corresponds to the outside thread 13 on the connecting piece 5, and the cylindrical section 14A is of a diameter, which corresponds to the outside diameter of the cylindrical sub-division 12B of the connecting piece 5. The conical section 14B of the bore 14 is of a conicity that corresponds to the conicity of the conical sub-division 12A of the connecting piece 5.

Following on from the bore 14 in the connecting piece 7 is a bore 16 which has a sub-division 16A of smaller diameter and a sub-division 16B of larger diameter. Seated in the sub-division 16B is the flexible tube 6 of the feeding probe 2, which is preferably adhesive-bonded and/or welded to the connecting piece 7.

To make a connection between the transfer system 1 and the feeding probe 2, their respective connecting pieces 5 and 7 are plugged together and screwed to one another. When this is done, the circumferential surface of the conical sub-division 12A seals against the circumferential surface of the conical section 14B, while the screwed connection stops the connecting pieces from being able to come loose unintentionally. It is also advantageous that the frictional and positively engaged connection is resistant to ageing because any fatigue or wear of the material can only have an effect in the long term.

Both a frictional and a positively engaged connection can be made with the connecting pieces 5 and 7. If the diameter of the front section 11D of the connecting piece 5 is selected to be so large that the connecting piece is not compatible with the female Luer connectors of catheters which are not intended for enteral feeding, then any mix-ups can be ruled out.

It is of advantage that the connecting piece 5 of the transfer system 1 can be connected not only to the connecting piece 7 of the feeding probe 2, which connecting piece 7 was described by reference to FIGS. 2a and 2b, but similarly can also be connected to funnel-shaped connecting pieces of different diameters of known feeding probes.

Figure 3A:
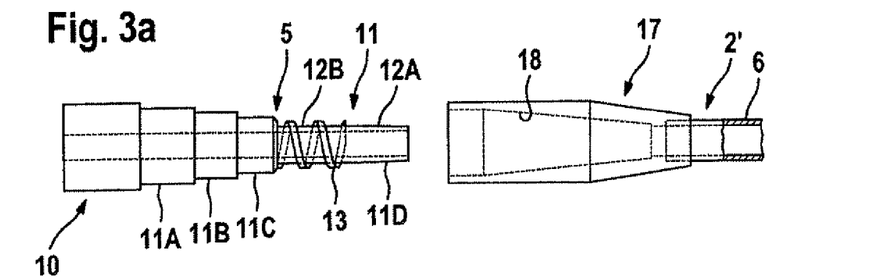
FIGS. 3a and 3b are enlarged views of the connecting piece of the transfer system shown in FIG. 1 and a funnel-shaped connecting piece of a known feeding probe, before and after the making of a connection between the transfer system and the feeding probe.
Figure 3B:
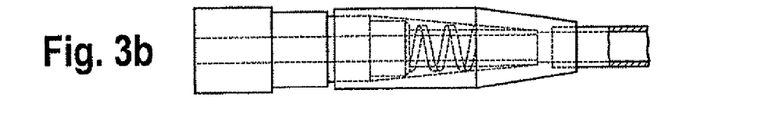

FIGS. 3a and 3b show the connection of the connecting piece 5 of the transfer system to a funnel-shaped connecting piece 17 of a known feeding probe 2'. The funnel-shaped connecting piece 17 has a funnel-shaped bore 18 which is shown in broken lines. The connecting pieces 5 and 17 are plugged together until the connecting piece 5 is firmly seated in the funnel-shaped bore 18 in the connecting piece 17. When this is done, the circumferential surface of at least one of the sections 11A, 11B, 11C, 11D seal against the circumferential surface of the funnel-shaped bore 18. However, compared with the screwed connection, this connection does have the disadvantage that it is possible for the connecting pieces to come loose unintentionally if the connection is stressed in traction.

Figure 4A:
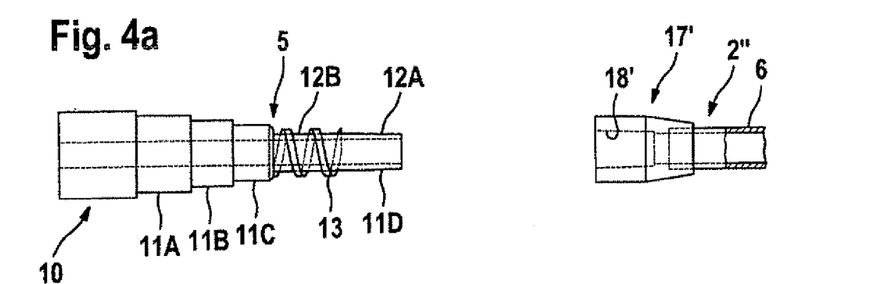
FIGS. 4a and 4b show the connecting piece of the transfer system shown in FIG. 1 and a funnel-shaped connecting piece of another known feeding probe, the latter connecting piece being of a smaller diameter than the connecting piece of the feeding probe shown in FIGS. 3a and 3b.
Figure 4B:
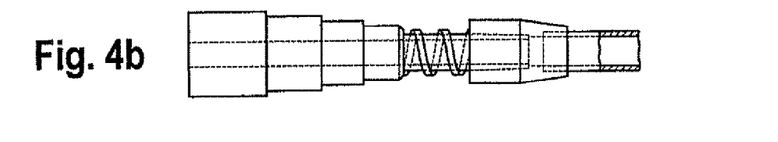

FIGS. 4a and 4b make it clear that it is possible for the connecting piece 5 of the transfer system 1 also to be to a funnel-shaped connecting piece 17' of a known feeding probe 2", which differs in size from the connecting piece 17 of the feeding probe which is shown in FIGS. 3A and 3b. The probe 2" has a smaller connecting piece 17' than the probe 2'. The known pediatric probes for example have a connecting piece 17' of this kind. In the connection which is shown in FIGS. 4A and 4b, the conical sub-division 12A of the connecting piece 5 seats in the funnel-shaped bore 18' in the connecting piece 17'.

Figure 5A:
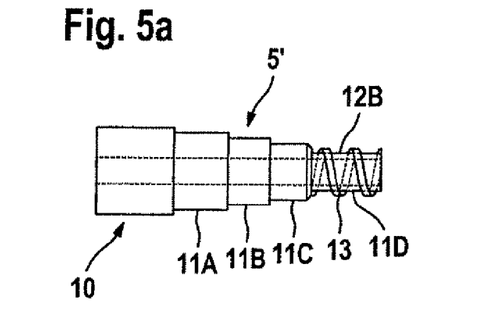
FIGS. 5a and 5b show an alternative embodiment of the connecting pieces of the transfer system and the feeding probe.
Figure 5B:
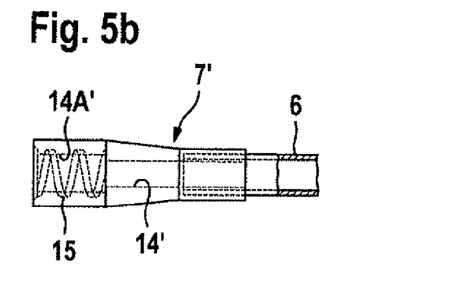

FIGS. 5a and 5b show a further embodiment of the connecting piece 5' of the transfer system 1 which differs from the embodiment which was described by reference to FIGS. 2a and 2b only in that the front section 11D of the connecting piece does not have the conical sub-division 12A but only the cylindrical sub-division 12B having the outside thread 13. The connecting pieces 5 and 5' are otherwise identical. Parts which correspond to one another have therefore been identified by the same reference numerals. The connecting piece 5' of the transfer system 1 is connected to the connecting piece 7' of the feeding probe, which connecting piece 7' is shown in FIG. 5b. The connecting piece 7' differs from the connecting piece 7 shown in FIGS. 2a and 2b in that the bore 14' has only the sub-division 14A' having the inside thread 15 but not the conical sub-division. However, it is also possible for the connecting piece 5' to be screwed to the connecting piece 7 shown in FIGS. 2a and 2b.

In the embodiment shown in FIG. 5a and FIG. 5b, the seal is made by pressing the end-faces of the connecting piece 7' on the flexible probe tube 6 and of the connecting piece 5' of the transfer system 1 together when the connecting pieces are screwed together. It is however also possible for a seal to be made by means of the thread.

Figure 6:
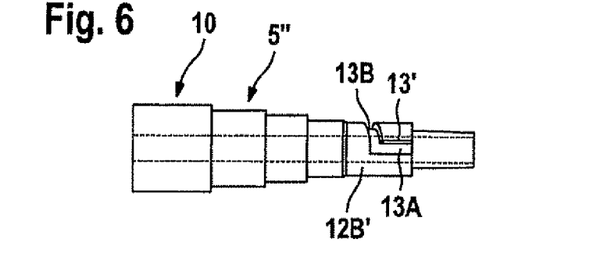
FIG. 6 shows a further alternative embodiment of the connecting piece of the transfer system.

FIG. 6 shows a further embodiment of the connecting piece 5" of the transfer system 1 which differs from the embodiment shown in FIGS. 2a and 2b in that the cylindrical sub-division 12B' is in the form of a bayonet-type connecting element. This bayonet-type connecting element has, instead of the outside thread 13, a groove 13' in the circumferential surface of the cylindrical sub-division, which groove 13' has an axially extending section 13A connected to a section 13B which extends part-way round the circumference of the circumferential surface. The connecting piece 5" can be connected by friction and positive engagement to a connecting piece (not shown) of a feeding probe 6 which, instead of having an inside thread, has on the inside face of the bore, a projection which engages in the groove 13'. For connecting purposes, the connecting pieces of the transfer system and the feeding probe are first slid together and then turned relative to one another.

Figure 7:
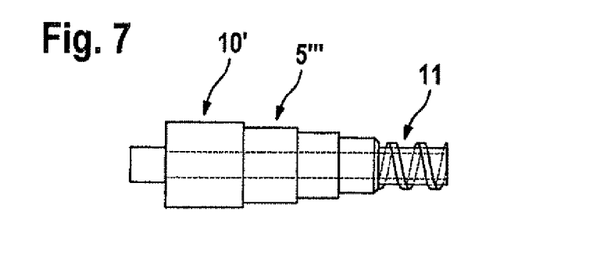
FIG. 7 shows a further alternative embodiment of the connecting piece of the transfer system.

FIG. 7 shows a further embodiment of the connecting piece 5''' of the transfer system 1 that differs from the embodiment shown in FIG. 5a only in that the proximal connecting portion 10 for the distal end of the flexible connecting tube 3 of the transfer system 1 does not take the form of a connecting portion to which the flexible connecting tube is solidly connected, being welded or adhesive-bonded for example, but takes the form of a luer lock connecting portion 10' to which the complementary luer lock connecting portion on the distal end of the flexible connecting tube of the transfer system can be connected. Complementary luer lock connecting portions of this kind, which are referred to as male and female luer lock connecting portions, are generally known per se to the person skilled in the art.

Figure 8A:
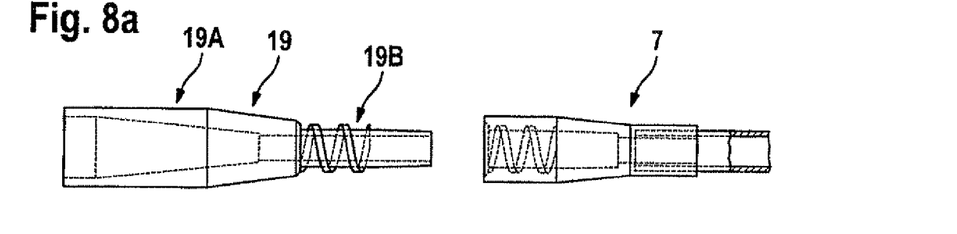
FIGS. 8a and 8b are enlarged views of the connecting piece of the feeding probe shown in FIG. 1 and of an adapter for the connecting piece, before and after the making of a connection between the connecting piece and adapter.
Figure 8B:
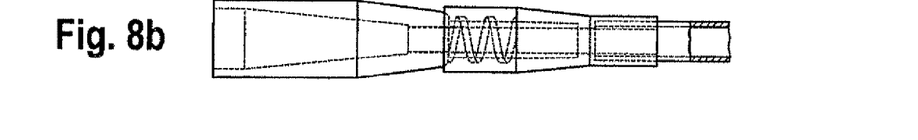

In the event that use should be made of a feeding probe that has the connecting piece 7 shown in FIGS. 2a and 2b and that the connecting piece according to the present invention should not be available for the transfer system, a transfer system having a conventional connecting piece can be connected to the connecting piece 7 of the feeding probe if the adapter 19 shown in FIGS. 8a and 8b is used. The adapter 19 has a funnel-shaped portion 19A which corresponds to the adapter of known feeding probes, and has a cylindrical portion 19B which corresponds to the front sub-division 11D which has the cylindrical section 12B having the outside thread 13 and the conical section 12A (FIGS. 2a and 2b). If the adapter 19 is screwed to the connecting piece 7, the feeding probe can be connected to known transfer systems having the conventional connecting pieces.

Figure 9:
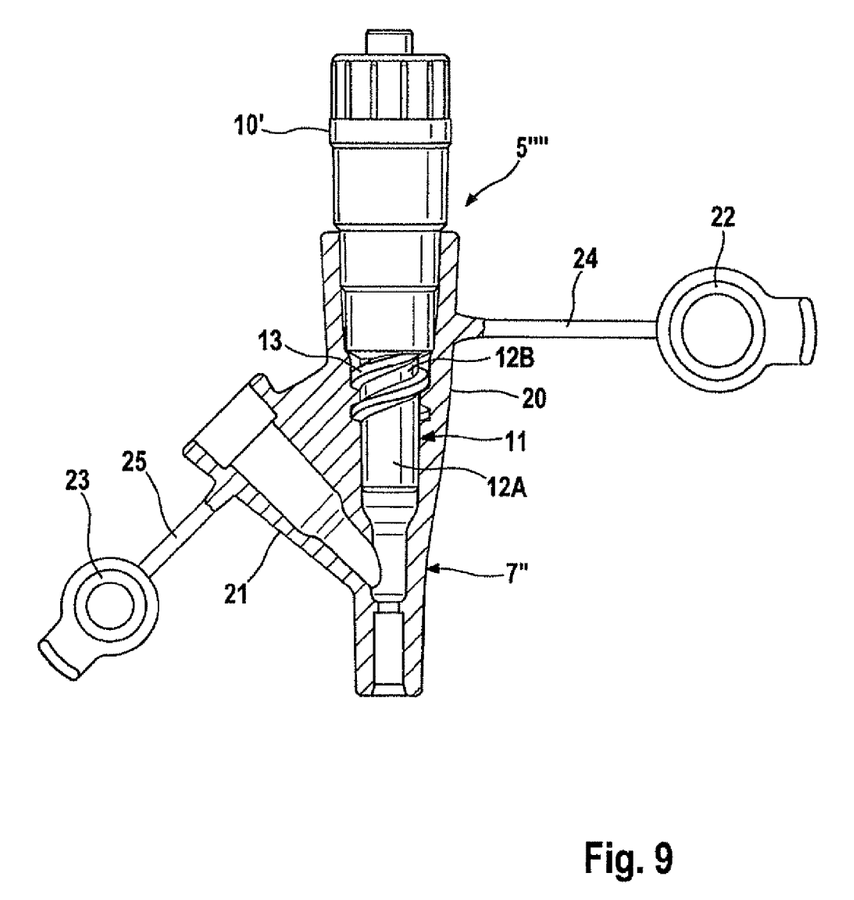
FIG. 9 shows a further embodiment of the connecting piece according to the present invention together with the connecting piece of the flexible probe tube.

FIG. 9 is a view partly in section showing a further embodiment of the connecting piece according to the present invention of the transfer system, together with the connecting piece of the flexible probe tube. As in the embodiment shown in FIG. 7, the connecting piece 5'''' of the transfer system has a luer lock connecting portion 10' for connecting on the distal end of the flexible connecting tube of the transfer system. The embodiment shown in FIG. 9 differs from the embodiment shown in FIG. 7 in that the section of smallest diameter, which takes the form of a locking element 11, has not only a cylindrical connecting element 12B having an outside thread 13 but also a distal connecting cone 12A which follows on from the connecting element.

The connecting piece 7'' on the flexible probe tube has a first connecting funnel 20 from which a second connecting funnel 21 branches off. The first connecting funnel 20 is used to connect on the connecting piece 5'''' of the transfer system, whereas the second connecting funnel 21 is used to connect on a further connecting portion although this is not shown in FIG. 9. Closing-off caps 22, 23 which are integrally formed on the connecting piece by means of bridges 24, 25 are provided to allow the connecting funnels to be closed off. FIG. 9 shows that the stepped section of the connecting piece 5'''' of the transfer system is firmly seated in the first connecting funnel 20 of the connecting piece 7'' of the flexible probe tube with a seal.

Figure 10:
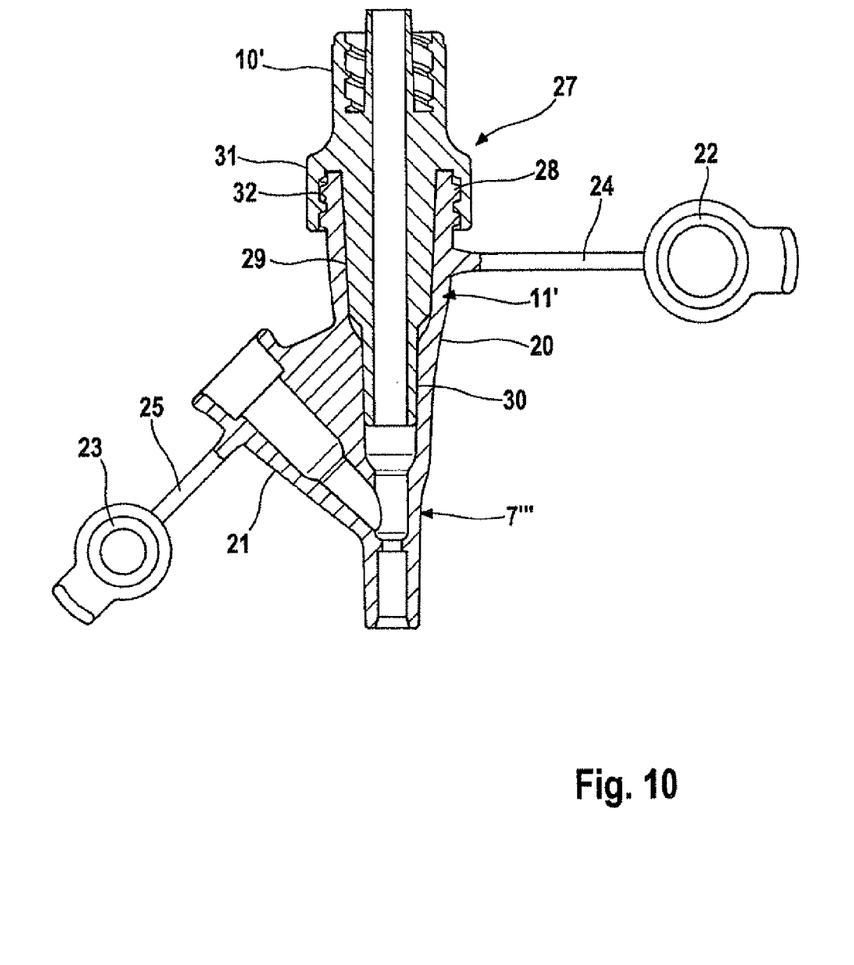
FIG. 10 shows an embodiment of an alternative form of the connecting piece according to the present invention together with the connecting piece of the flexible probe tube.

FIG. 10 is a view in section of an embodiment of an alternative form of the connecting piece 27 according to the invention together with the connecting piece 7''' of the flexible probe tube, which connecting piece 7''' once again has the two connecting funnels 20, 21. The connecting piece 7''' corresponds to the connecting piece 7'' shown in FIG. 9 except that the first connecting funnel 20 shown in FIG. 10 has an outside thread 28. The embodiment shown in FIG. 10 also differs from the embodiment shown in FIG. 9 in respect of the connecting piece 27 to which the flexible tubing line of the transfer system is connected.

The connecting piece 27 has, as a proximal connecting portion for the flexible tubing line of the transfer system, a luer lock connecting portion 10', which is known per se to the person skilled in the art. Following on from the luer lock connecting portion 10' there is the distal connecting portion 11', which is connected to the first connecting funnel 20.

In the present embodiment, the distal connecting portion 11' does not have a stepped section but a conical section 29 which merges into a connecting cone 30 which is of smaller diameter than the conical section. The conical section 29 of the distal connecting portion seats in the upper section of larger inside diameter of the first connecting funnel 20, whereas the conical connecting cone 30 seats in the lower section of smaller inside diameter of the connecting funnel 20. As a result the two parts are sealed against one another.

To secure the connecting piece 27 to the connecting funnel 20, the distal connecting portion 11' has, in this embodiment too, a locking element, which in this case takes the form of a screwed cap 31 having an inside thread 32, which screwed cap 31 encloses the conical section 29 of the connecting piece 27 for part of its length. The screwed cap 31 can be screwed to the connecting funnel 20, and the two parts are thus releasably connected to one another.

The invention claimed is:

1. A first connecting piece for an enteral transfer system, comprising:
    a proximal connecting portion for connection to a flexible connecting tube of a transfer system; and
    a distal connecting portion for connection to a second connecting piece of a flexible tube of an enteral feeding probe,
    said distal connecting portion being of a conical form, or a stepped form having a plurality of sections of different diameters, adapted to enable a releasable connection to be made to funnel-shaped connecting pieces having different diameters of the flexible tubes of enteral feeding probes,
    said distal connecting portion comprising a first locking element configured such that a positively engaging releasable connection can be made to the second connecting piece having a second locking element that is complementary to the first locking element,
    wherein the distal connecting portion comprises a front conical part forming a distal connecting cone, and a back part proximally adjoining inline with the front conical part and forming the first locking element;
    wherein the first locking element is a screwed connecting element having an outside thread for making the positively engaging releasable connection.

2. The first connecting piece of claim 1, wherein the section of the plurality of sections that is of the smallest diameter takes the form of the first locking element.

3. The first connecting piece of claim 1, wherein the proximal connecting portion is configured to make a releasable connection to a complementary connecting portion of the transfer system.

4. The first connecting piece of claim 1, wherein the proximal connecting portion is a luer lock connecting portion.

5. A transfer system for enteral feeding comprising the first connecting piece of claim 1 and a flexible connecting tube having a distal end and a proximal end, wherein the proximal connecting portion of the first connecting piece is solidly connected to the distal end of the flexible connecting tube.

6. A system comprising the transfer system of claim 5, further comprising:
    an enteral feeding probe comprising: a flexible probe tube and a second connecting piece for connection to the transfer system,
    wherein the second connecting piece has a second locking element that is complementary to the first locking element of the first connecting piece.

7. The system of claim 6, wherein the second connecting piece of the flexible probe tube and the first connecting piece of the transfer system are scaling screwed connectors.

8. The system of claim 7, wherein the second connecting piece of the flexible probe tube comprises a connecting funnel having an outside thread.

* * * * *

UNITED STATES PATENT AND TRADEMARK OFFICE
CERTIFICATE OF CORRECTION

PATENT NO. : 8,500,717 B2  
APPLICATION NO. : 12/447017  
DATED : August 6, 2013  
INVENTOR(S) : Michael Becker It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 611 days.

Signed and Sealed this

Fifteenth Day of September, 2015

Michelle K. Lee
*Director of the United States Patent and Trademark Office*